United States Patent
Séguy et al.

(10) Patent No.: US 12,383,541 B2
(45) Date of Patent: *Aug. 12, 2025

(54) ALK2 INHIBITORS FOR THE TREATMENT OF ANEMIA

(71) Applicant: Incyte Corporation, Wilmington, DE (US)

(72) Inventors: Francis Séguy, Lausanne (CH); Ekaterine Asatiani, Founex (CH); Yaoyu Chen, Newark, DE (US)

(73) Assignee: Incyte Corporation, Wilmington, DE (US)

( * ) Notice: Subject to any disclaimer, the term of this patent is extended or adjusted under 35 U.S.C. 154(b) by 77 days.

This patent is subject to a terminal disclaimer.

(21) Appl. No.: 18/343,267

(22) Filed: Jun. 28, 2023

(65) Prior Publication Data

US 2023/0338352 A1    Oct. 26, 2023

Related U.S. Application Data

(63) Continuation of application No. 17/348,102, filed on Jun. 15, 2021, now Pat. No. 11,723,899.

(60) Provisional application No. 63/152,516, filed on Feb. 23, 2021, provisional application No. 63/056,761, filed on Jul. 27, 2020, provisional application No. 63/039,742, filed on Jun. 16, 2020.

(51) Int. Cl.
*A61K 31/4439* (2006.01)
*A61K 9/00* (2006.01)
*A61P 7/06* (2006.01)

(52) U.S. Cl.
CPC ........ *A61K 31/4439* (2013.01); *A61K 9/0053* (2013.01); *A61P 7/06* (2018.01)

(58) Field of Classification Search
CPC .................................................. A61K 31/4439
See application file for complete search history.

(56) References Cited

U.S. PATENT DOCUMENTS

| | | | |
|---|---|---|---|
| 5,077,290 A | 12/1991 | Fisher et al. | |
| 6,090,812 A | 7/2000 | Feenstra et al. | |
| 7,015,227 B2 | 3/2006 | Darrow et al. | |
| 7,595,321 B2 | 9/2009 | Berg et al. | |
| 10,196,392 B2 | 2/2019 | Hopkins et al. | |
| 10,202,356 B2 | 2/2019 | Mollard et al. | |
| 10,710,980 B2 * | 7/2020 | Arista | C07D 401/14 |
| 10,947,218 B2 * | 3/2021 | Arista | C07D 401/14 |
| 11,723,899 B2 * | 8/2023 | Seguy | A61P 7/06 |
| | | | 514/339 |
| 2004/0067985 A1 | 4/2004 | Haviv et al. | |
| 2004/0265909 A1 | 12/2004 | Blaney et al. | |
| 2006/0052396 A1 | 3/2006 | Berg et al. | |
| 2007/0197564 A1 | 8/2007 | Lavey et al. | |
| 2008/0021024 A1 | 1/2008 | Sucholeiki et al. | |
| 2008/0153850 A1 | 6/2008 | Ford et al. | |
| 2011/0294836 A1 | 12/2011 | Song et al. | |
| 2012/0225851 A1 | 9/2012 | Cardone et al. | |
| 2014/0142097 A1 | 5/2014 | Hoelzemann et al. | |
| 2014/0328756 A1 | 11/2014 | Radeke et al. | |
| 2016/0115167 A1 | 4/2016 | Yu et al. | |
| 2016/0264548 A1 | 9/2016 | Qui et al. | |
| 2017/0066742 A1 | 3/2017 | Kim et al. | |
| 2018/0009754 A1 | 1/2018 | Long et al. | |
| 2021/0154195 A1 | 5/2021 | Chen et al. | |

FOREIGN PATENT DOCUMENTS

| | | |
|---|---|---|
| EP | 1875912 A1 | 1/2008 |
| WO | WO 2003/093297 A2 | 11/2003 |
| WO | WO 2005/115985 A1 | 12/2005 |
| WO | WO 2007/011760 A2 | 1/2007 |
| WO | WO 2018/014829 A1 | 1/2018 |
| WO | WO 2018/106820 A1 | 6/2018 |
| WO | WO 2021/062163 A1 | 4/2021 |
| WO | WO 2021/062171 A1 | 4/2021 |
| WO | WO 2021/102258 A1 | 5/2021 |

OTHER PUBLICATIONS

Backus et al., "Selective inhibition of ALK2 signaling ameliorates disease in a novel model of iron refractory iron deficiency (IRIDA)", *Hemasphere* vol. 4, Supplement 1 (2020).
HOPKINS; "Inhibitors of the bone morphogenetic protein (BMP) signaling pathway: a patent review", *Expert Opinion on Therapeutic Patents* 26(10):1115-1128 (2006).
Kim et al., "Identification of novel ALK2 inhibitors and their effect on cancer cells", *Biochemical and Biophysical Research Communications* 492:121-127 (2017).
Mohedas et al., "Development of an ALK2-biased BMP type I receptor kinase inhibitor", *ACS Chemical Biology* 8(6):1291-1302 (2013).
Mohedas et al., "Structure-Activity Relationship of 3,5-Diaryl-2-aminopyridine ALK2 Inhibitors Reveals Unaltered Binding Affinity for Fibrodysplasia Ossificans Progressiva Causing Mutants", *Journal of Medicinal Chemistry* 57(19): 7900-7915 (2014).

(Continued)

*Primary Examiner* — Rei Tsang Shiao
(74) *Attorney, Agent, or Firm* — Lathrop GPM LLP; Brian C. Trinque; Nicole Sassu

(57) ABSTRACT

Provided herein are methods of treating anemia in a subject in need thereof comprising administering to the subject a therapeutically effective amount of an ALK2 inhibitor.

25 Claims, 2 Drawing Sheets

(56) References Cited

OTHER PUBLICATIONS

Notification of Transmittal of The International Search Report and The Written Opinion of the International Searching Authority, or the Declaration, issued on Oct. 24, 2017 in International Application No. PCT/CN2017/093385, International Filing Date: Jul. 18, 2017.
Notification of Transmittal of The International Search Report and The Written Opinion of the International Searching Authority, or the Declaration, issued on Dec. 23, 2021 in International Application No. PCT/US2021/037377, International Filing Date: Jun. 15, 2021.
Peterson et. al., "TP-0184 Inhibits ALK2/ACVR1, Decreases Hepcidin Levels, and Demonstrates Activity in Preclinical Mouse Models of Functional Iron Deficiency", *Blood* 130:937 (2017).
Wontak et al., "Novel Series of ALK2 Inhibitors That Alter Hepcidin Expression as Potential Therapeutics for Anemia of Chronic Disease", *Blood* 124(21):212 (2014).
Asshoff et al., "The Jak1/Jak2 Inhibitor Momelotinib Inhibits Alk2, Decreases Hepcidin Production and Ameliorates Anemia of Chronic Disease (ACD) in Rodents", *Blood* 126(3):538 (2015).

* cited by examiner

ALK2 INHIBITORS FOR THE TREATMENT OF ANEMIA

RELATED APPLICATIONS

This application is a continuation of U.S. patent application Ser. No. 17/348,102, filed Jun. 15, 2021, which claims priority to U.S. Provisional Application No. 63/152,516 filed on Feb. 23, 2021, U.S. Provisional Application No. 63/056,761 filed on Jul. 27, 2020, and U.S. Provisional Application No. 63/039,742 filed on Jun. 16, 2020, the contents of which are hereby incorporated in their entireties.

BACKGROUND

Myelodysplastic syndromes (MDS) are clonal stem disorders characterized by ineffective hematopoiesis, morphological dysplasia, peripheral blood cytopenias, and a high risk of progression to acute myelogenous leukemia. The majority of patients present with low- or intermediate-risk MDS, as defined by the International Prognostic Scoring System criteria. Anemia is a major therapeutic challenge in these patients with MDS and is present in 85% of them. The pathophysiology of anemia in MDS may overlap with the pathophysiology of anemia of inflammation, particularly in early-stage (i.e., lower-risk) MDS. In many patients with MDS, levels of pro-inflammatory cytokines, e.g., in IL-6, have been shown to induce the synthesis of hepcidin during inflammation. For those patients, the standard of care primarily comprises supportive care for their symptoms: RBC transfusions and ESAs for anemic patients and management of risk of bleeding and infections. Chronic anemia and RBC transfusions are independent risk factors affecting survival and are associated with iron overload, fatigue, impaired quality of life, and increased cardiovascular risks. ESAs can provide clinical benefit to some patients with MDS. However, only approximately 30% of patients treated with ESAs achieve improvement. The benefit is usually limited to a minority of patients that have low erythropoietin level at baseline. The majority of patients have elevated serum erythropoietin concentrations, which indicates that anemia in MDS is due to ineffective erythropoiesis that often cannot be corrected by exogenous ESA administration. Treatment of anemia and reduction of transfusion burden are the major therapeutic goals in patients with low- or intermediate-risk MDS. There are few treatment options for these patients, particularly after failure of ESA.

Anemia also impacts those suffering from multiple myeloma (MM): nearly all patients with MM will be affected by anemia during the course of their disease. Multiple myeloma is a malignant plasma cell dyscrasia characterized by a clonal proliferation of plasmatic cells in bone marrow, and monoclonal gammopathy. Symptomatic patients and their need for therapy are defined by the presence of hypercalcemia (C), renal insufficiency (R), anemia (A), and/or bone lesions (B) according to the CRAB criteria (Kyle, R. A.; Rajkumar, S.V. *Leukemia* 2009; 23:3-9). A retrospective study of 1,027 MM patients in the U.S. demonstrated that anemia (hemoglobin concentration <120 g/l) was present at diagnosis in 73% of patients (Kyle et al 2003, Mayo Clin Proc. 2003; 78:21-33). A European wide survey in 720 patients with MM showed that 29.7% of the patients present with hemoglobin levels of ≤9.9 g/dL at time of diagnosis, 85.3% of these patients were anemic at any time during the survey (Birgegard G, et al. *Eur J Haematol.* 2006; 77:378-386). Approximately 10% of MM patients have a value of hemoglobin below 8 g/dL (VanderWall K, et al. *Crit. Rev. Oncog.* 2013; 18:449-461). Nonresponders and relapsing myeloma patients often continue to suffer from anemia.

Anemia also represents a challenge in the management of patients with myelofibrosis (MF): 35-54% of patients with MF are reported to have hemoglobin levels <10 g/dL and approximately 25% of these patients are dependent on red blood cell (RBC) transfusion at the time of diagnosis. Elevated serum hepcidin levels have been shown to be associated with reduced hemoglobin, increased requirement for RBC transfusions, and reduced overall survival in patients with MF. Anemia is also a common complication of chronic kidney disease (CKD). The current management of patients with anemia in CKD is controversial, with recent clinical trials demonstrating increased morbidity and mortality related to erythropoiesis stimulating agents.

There remains a need for new treatments of anemia, especially anemia associated with MDS, MM, CKD, or MF.

SUMMARY

Provided herein is a method of treating anemia in a subject in need thereof, comprising administering to the subject a compound of Formula I:

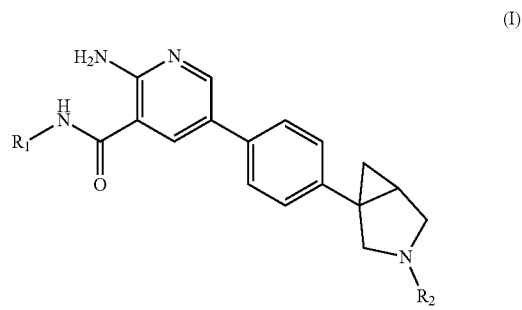

(I)

or a pharmaceutically acceptable salt thereof, wherein the variables are defined herein.

In the method provided herein, $R_1$ of the compound of Formula I can be bridged $C_8$-cycloalkyl substituted with hydroxy. Further, $R_2$ of the compound of Formula I can be tetrahydropyran.

The compound of Formula I can be the compound 2-amino-N-(4-hydroxybicyclo[2.2.2]octan-1-yl)-5-(4-(3-(tetrahydro-2H-pyran-4-yl)-3-azabicyclo[3.1.0]hexan-1-yl)phenyl)nicotinamide, or a pharmaceutically acceptable salt thereof.

The compound of Formula I can also be 2-amino-N-(4-hydroxybicyclo-[2.2.2]octan-1-yl)-5-(4-((1R,5S)-3-(tetrahydro-2H-pyran-4-yl)-3-azabicyclo[3.1.0]hexan-1-yl)phenyl)nicotinamide, or a pharmaceutically acceptable salt thereof.

The compound of Formula I can also be 2-amino-N-(4-hydroxybicyclo[2.2.2]octan-1-yl)-5-(4-((1S,5R)-3-(tetrahydro-2H-pyran-4-yl)-3-azabicyclo[3.1.0]hexan-1-yl)phenyl)nicotinamide, or a pharmaceutically acceptable salt thereof.

The compound of Formula I can also be 2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide fumarate dihydrate.

In the method of treating anemia provided herein, the subject can suffer from a myelodysplastic syndrome (MDS). The myelodysplastic syndrome (MDS) can be selected from the group consisting of MDS with multilineage dysplasia (MDS-MLD), MDS with single lineage dysplasia (MDS-SLD), MDS with excess blasts (MDS-EB), MDS with isolated del(5q), and MDS unclassifiable (MDS-U).

In addition, in the method of treating anemia provided herein, the subject can suffer from multiple myeloma (MM). The subject can also be transfusion-dependent or not transfusion-dependent.

The subject in the method of treating anemia can also suffer from myelodysplastic syndrome and myeloproliferative neoplasms (MDS/MPN) overlap syndromes such as chronic myelomonocytic leukemia (CMML) and unclassifiable MDS/MPN overlap syndromes.

The anemia of the method provided herein can be iron-refractory iron deficiency anemia (IRIDA).

In the method of treating anemia provided herein, the subject can suffer from myelofibrosis (MF). The subject suffering from MF can be transfusion-dependent or not transfusion-dependent.

The compound of Formula I can be administered orally. The compound of Formula I can also be administered as a monotherapy for the treatment of anemia. This compound can be administered at a dose of about 5 mg to about 500 mg once daily (QD), or more particularly at a dose of about 50 mg once daily (QD). The compound of Formula I can be administered as a 5 mg, 25 mg, or 50 mg tablet, or a combination thereof.

Also provided herein is a method of reducing hepcidin levels in a subject in need thereof, comprising administering to the subject a compound of Formula I, or a pharmaceutically acceptable salt thereof.

The subject of the method of reducing hepcidin levels can suffer from anemia. The anemia can be iron-refractory iron deficiency anemia (IRIDA). The subject can be either transfusion-dependent or not transfusion-dependent.

Also provided herein is a method of reducing hepcidin levels in a subject suffering from a myelodysplastic syndrome (MDS). The myelodysplastic syndrome (MDS) can be selected from the group consisting of MDS with multilineage dysplasia (MDS-MLD), MDS with single lineage dysplasia (MDS-SLD), MDS with excess blasts (MDS-EB), MDS with isolated del(5q), and MDS unclassifiable (MDS-U).

The subject of the method of reducing hepcidin levels can suffer from multiple myeloma (MM). The subject of the method of reducing hepcidin levels can suffer from myelofibrosis (MF). The subject of the method of reducing hepcidin levels can suffer from myeloproliferative neoplasms (MPN). The subject of the method of reducing hepcidin levels can suffer from chronic kidney disease (CKD).

When reducing hepcidin levels in a subject in need thereof, the compound of Formula I can be administered orally. The compound of Formula I can also be administered as a monotherapy for the treatment of anemia. This compound can be administered at a dose of about 5 mg to about 500 mg once daily (QD), or more particularly at a dose of about 50 mg once daily (QD). The compound of Formula I can be administered as a 5 mg, 25 mg, or 50 mg tablet, or any combination thereof.

DETAILED DESCRIPTION

Figure 1:
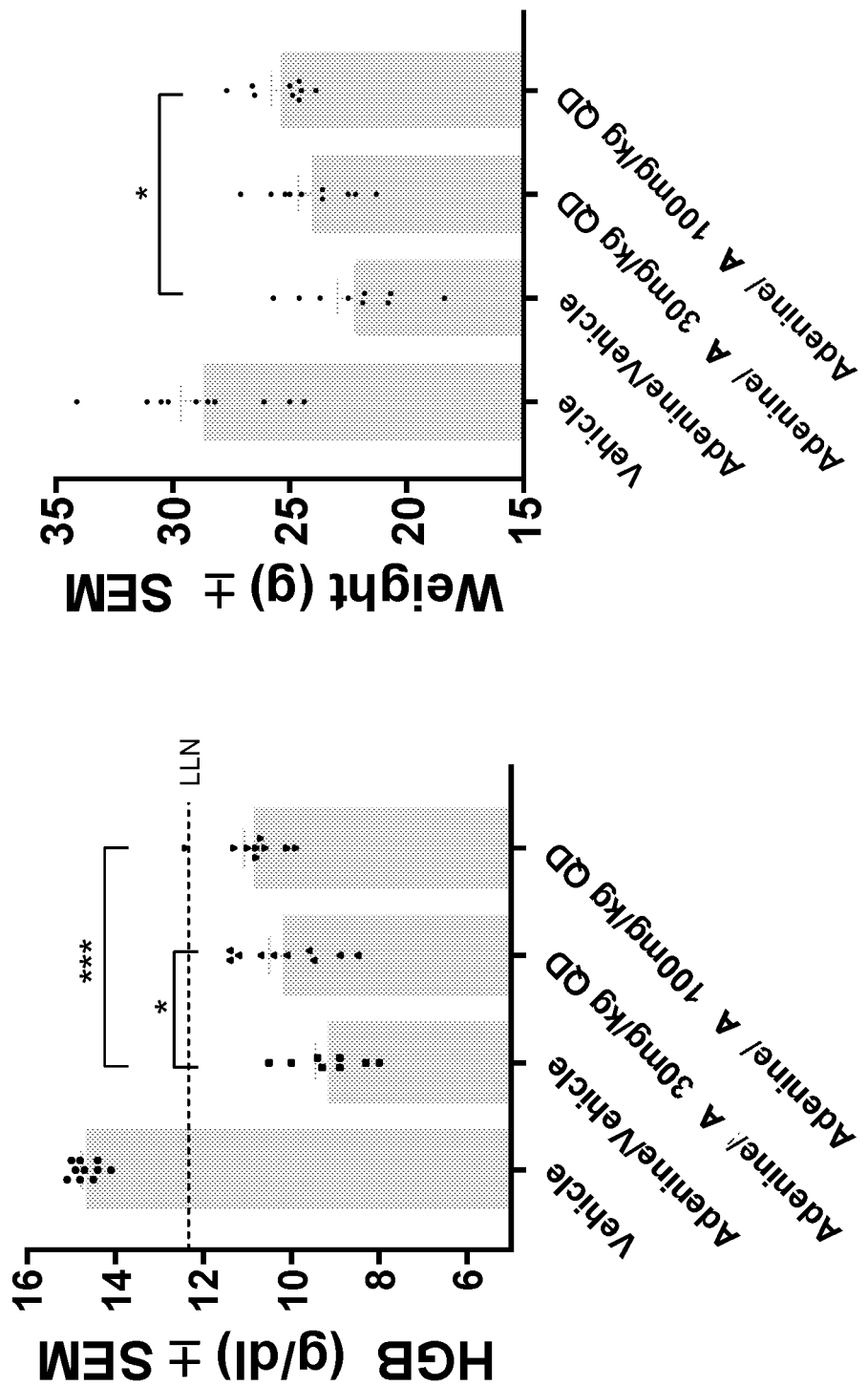
FIG. 1 shows the results of the mouse adenine-induced chronic kidney disease model where *p<0.05; p<0.01; *p<0.001 one way ANOVA with Tukey's multiple comparisons test, LLN=Lower limit of normal.

Provided herein is a method of treating anemia in a subject in need thereof, comprising administering to the subject a compound of Formula I, or a pharmaceutically acceptable salt thereof. Anemia is characterized by a decrease in number of red blood cells, or less than the normal quantity of hemoglobin in the blood. Anemia can also be caused by decreased oxygen-binding ability of the hemoglobin.

Also provided herein is a method of reducing hepcidin levels in a subject in need thereof, comprising administering to the subject a compound of Formula I, or a pharmaceutically acceptable salt thereof. Hepcidin is a small peptide hormone primarily synthesized in hepatocytes that reduces both duodenal iron absorption and iron export from monocytes and macrophages by binding to and inducing the internalization and degradation of the iron exporter ferroportin (Nemeth E, et al. *Science*. 2004; 306:2090-2093; Theurl I, et al. *Haematologica*. 2011; 96:1761-1769, Zhao N, Zhang A S, et al. *J Clin Invest*. 2013; 123(6):2337-2343). The elevated serum hepcidin levels enhance storage of iron within the reticuloendothelial system and result in reduced iron availability and iron restricted erythropoiesis. Inappropriately increased hepcidin expression causes severe functional iron deficiency anemia in humans and is central to the pathophysiology of anemia of chronic disease (Weiss G, Goodnough L T. *N Engl J Med* 2005; 352:1011-1023).

Inhibition of activin receptor-like kinase-2 (ALK2), an upstream regulator of hepcidin, should increase circulating iron levels, and improve anemia. The compounds provided herein have potent activity against the ALK2 kinase and inhibit bone morphogenetic protein (BMP)-induced hepcidin production.

Homeostatic control of hepcidin by iron was observed to be disrupted in most of MDS subtypes and almost completely lost in conditions with prominent dysmyelopoiesis like refractory anemia with excess blasts and in chronic myelomonocytic leukemia (CMML) (Santini V, et al. *PLoS ONE*. 2011; 6:e23109).

The cause of anemia in MM patients is probably multifactorial: BM infiltration by the myeloma itself leads to reduced numbers of erythroid precursors, erythropoietin deficiency (in patients with renal impairment), decreased responsiveness of the pro-erythroblasts and CFU-E cells to erythropoietin, impaired iron utilization due to increased production of hepcidin because of chronic inflammation, and paraprotein-induced increase of the plasma volume (König et al, *Clin Lymphoma Myeloma Leuk*. 2013; 13:671-680).

Serum hepcidin has been shown to be significantly higher in MM patients compared to healthy individuals and age-matched controls (Ibricevic-Balic et al, *Med Arch*. 2016 December; 70: 429-432; Victor et al, *Clin Lab*. 2017; 63:1273-1277; and Maes et al, *Blood*. 2010; 116:3635-3644). Patients with stage III MM at diagnosis had higher urinary hepcidin levels than normal controls. Hepcidin serum levels are inversely correlated with hemoglobin concentrations in MM patients (Katodritou et al, *Am J Hematol*. 2008; 83:697-701) and also in MM patients with normal renal function indicating a possible contribution of increased hepcidin to the pathogenesis of MM anemia (Maes et al, 2010). Furthermore, in myeloma patients with normal renal function, urinary hepcidin was inversely correlated with hemoglobin level at diagnosis, strongly suggesting a causal relationship between up-regulated hepcidin expression and anemia. The urinary hepcidin also significantly correlated with serum ferritin and C-reactive protein (Sharma et al, *Clin Cancer Res.* 2008; 14: 3262-3267).

Iron-refractory iron deficiency anemia (IRIDA) is a rare, inherited form of iron deficiency anemia. Iron deficiency anemia occurs when red blood cell counts are low due to a lack of iron. While iron deficiency anemia is generally an acquired disease due to insufficient iron in the person's diet or chronic blood loss, IRIDA is an autosomal recessive condition that results from mutations in TMPRSS6 gene, which causes iron deficiency (Bhatia, P, et al. *Pediatr. Hematol. Oncol. J.* 2017; 2; 48-53). Common forms of acquired iron deficiency anemia are commonly treated by oral iron supplements or intravenous (IV) iron infusions, but patients with IRIDA will not respond fully to those treatments.

Patients with myelofibrosis (MF) may develop splenomegaly (due to extramedullary hematopoiesis), hypercatabolic symptoms (due to overexpression of inflammatory cytokines), and anemia (due to bone marrow failure and splenic sequestration). MF remains curable mainly with allogeneic hematopoietic stem cell transplantation (ASCT), a therapy that few MF patients are deemed fit to undergo. The goals of treatment are thus often palliative. JAK inhibitors may provide a therapy to patients with MF; however, therapy-related anemia is often a downside to this treatment. Anemia thus remains a challenge in the management of MF and represents a major unmet need. Intractable anemia depresses quality of life, portends poor outcomes, and can act to restrict access to palliative JAK inhibition in some patients. While therapies for MF-related anemia do exist, they are limited in their efficacy, durability, and tolerability.

Anemia in CKD is typically normocytic, normochromic, and hypoproliferative. Anemia management was revolutionized in the late 1980s with the introduction of recombinant human EPO. This and related erythropoiesis stimulating agents (ESAs) greatly benefited patients by improving their debilitating symptoms, and freeing them from dependence on blood transfusions with their associated complications (secondary iron overload, infections, and sensitization impeding transplantation). However, even in the initial studies, adverse effects were noted in patients receiving ESAs, including worsening hypertension, seizures, and dialysis access clotting. In addition, ESAs do not reduce adverse outcomes associated with anemia, such as mortality, nonfatal cardiovascular events, left ventricular hypertrophy, hospitalizations, and progression of kidney disease, in prospective randomized controlled trials.

Therapies currently in development promise improved anemia-specific outcomes; however, are still early in the pathway to regulatory approval and regular clinical use.

Definitions

Listed below are definitions of various terms used herein. These definitions apply to the terms as they are used throughout this specification and claims, unless otherwise limited in specific instances, either individually or as part of a larger group. Unless defined otherwise, all technical and scientific terms used herein have the same meaning as is commonly understood by one of skill in the art to which this invention belongs. Compounds of the present disclosure are described using standard nomenclature.

Unless defined otherwise, all technical and scientific terms used herein generally have the same meaning as commonly understood by one of ordinary skill in the art. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, "pharmaceutical combination" or "combination" refers to formulations of the separate compounds with or without instructions for combined use or to combination products. The combination compounds may thus be entirely separate pharmaceutical dosage forms or in pharmaceutical compositions that are also sold independently of each other and where just instructions for their combined use are provided in the package equipment, e.g., leaflet or the like, or in other information, e.g., provided to physicians and medical staff (e.g. oral communications, communications in writing or the like), for simultaneous or sequential use for being jointly active.

As used herein, the term "treating" or "treatment" refers to inhibiting a disease; for example, inhibiting a disease, condition, or disorder in an individual who is experiencing or displaying the pathology or symptomology of the disease, condition, or disorder (i.e., arresting further development of the pathology and/or symptomology) or ameliorating the disease; for example, ameliorating a disease, condition, or disorder in an individual who is experiencing or displaying the pathology or symptomology of the disease, condition, or disorder (i.e., reversing the pathology and/or symptomology) such as decreasing the severity of the disease.

The term "prevent," "preventing," or "prevention" as used herein, comprises the prevention of at least one symptom associated with or caused by the state, disease or disorder being prevented.

As used herein, the term "patient," "individual," or "subject" refers to a human or a non-human mammal. Non-human mammals include, for example, livestock and pets, such as ovine, bovine, porcine, canine, feline and marine mammals. Preferably, the patient, subject, or individual is human.

As used herein, the phrase "transfusion dependent" means that a subject receives regular platelet and/or red blood cell (RBC) transfusions more frequently than every 8 weeks due to persistently low platelet and/or RBC counts.

As used herein, the phrase "transfusion independent" means that a subject does not receive platelet and/or red blood cell (RBC) transfusions for at least 8 consecutive weeks.

As used herein, the term "monotherapy" means that the treatment uses a single active pharmaceutical ingredient to treat a disease or condition. A monotherapy can still include treatment with a pharmaceutically acceptable carrier or excipient. In an embodiment of the methods provided herein, the single active pharmaceutical ingredient is a compound of Formula I. In another embodiment, a compound of Formula I is administered as a monotherapy not in conjunction with a Janus kinase inhibitor.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein a parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts described herein include the conventional non-toxic salts of the parent compound formed, for example, from non-toxic inorganic or organic acids. The pharmaceutically acceptable salts discussed herein can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are used. The phrase "pharmaceutically acceptable salt" is not limited to a mono, or 1:1, salt. For example, "pharmaceutically acceptable salt" also includes bis-salts, such as a bis-hydrochloride salt. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound with a pharmaceutically acceptable carrier. The pharmaceutical composition facilitates administration of the composition to a patient or subject. Multiple techniques of administering a compound exist in the art including, but not limited to, intravenous, oral, aerosol, parenteral, ophthalmic, pulmonary, and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound disclosed herein, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of a compound disclosed herein, and are physiologically acceptable to the patient. Supplementary active compounds may also be incorporated into the compositions. The "pharmaceutically acceptable carrier" may further include a pharmaceutically acceptable salt of the compound(s) disclosed herein. Other additional ingredients that may be included in the pharmaceutical compositions are known in the art and described, for example, in Remington's Pharmaceutical Sciences (Genaro, Ed., Mack Publishing Co., 1985, Easton, PA), which is incorporated herein by reference.

As used herein, the term "ALK2" or "ALK-2" refers to activin A receptor, type I (ACVRI), also known as ACVRLK2; SKR1; ACVR1A; Activin receptor type I; Activin receptor-like kinase 2; Serine/threonine-protein kinase receptor R1; TGF-B superfamily receptor type I; ACTRI; TSRI; activin A receptor, type II-like kinase 2; activin receptor type-1; hydroxyalkyl-protein kinase; ACTR-I; TSR-I. Therefore, an "ALK2 inhibitor," as used herein, refers to a compound that modulates the activity of ALK2.

The term "single formulation" as used herein refers to a single carrier or vehicle formulated to deliver effective amounts of both therapeutic agents to a patient. The single vehicle is designed to deliver an effective amount of each of the agents, along with any pharmaceutically acceptable carriers or excipients. In some embodiments, the vehicle is a tablet, capsule, pill, or a patch. In other embodiments, the vehicle is a solution or a suspension.

The term "unit dose" is used herein to mean simultaneous administration of both agents together, in one dosage form, to the patient being treated. In some embodiments, the unit dose is a single formulation. In certain embodiments, the unit dose includes one or more vehicles such that each vehicle includes an effective amount of at least one of the agents along with pharmaceutically acceptable carriers and excipients. In some embodiments, the unit dose is one or more tablets, capsules, pills, or patches administered to the patient at the same time.

An "oral dosage form" includes a unit dosage form prescribed or intended for oral administration.

As used herein, the term "alkyl," by itself or as part of another substituent means, unless otherwise stated, a straight or branched chain hydrocarbon having the number of carbon atoms designated (i.e., $C_1$-$C_6$-alkyl means an alkyl having one to six carbon atoms) and includes straight and branched chains. In an embodiment, $C_1$-$C_3$, $C_1$-$C_4$, $C_1$-$C_6$alkyl groups are provided herein. Examples include methyl, ethyl, propyl, isopropyl, butyl, isobutyl, tert-butyl, pentyl, neopentyl, and hexyl.

As used herein, the term "alkenyl" refers to a monovalent group derived from a hydrocarbon moiety containing, in certain embodiments, from two to four, two to six, or two to eight carbon atoms having at least one carbon-carbon double bond. The alkenyl group may or may not be the point of attachment to another group. The term "alkenyl" includes, but is not limited to, ethenyl, 1-propenyl, 1-butenyl, heptenyl, octenyl and the like.

As used herein, the term "alkynyl" refers to a monovalent group derived from a hydrocarbon moiety containing, in certain embodiments, from two to four, two to six, or two to eight carbon atoms having at least one carbon-carbon triple bond. The alkynyl group may or may not be the point of attachment to another group. The term "alkynyl" includes, but is not limited to, ethynyl, 1-propynyl, 1-butynyl, heptynyl, octynyl and the like.

As used herein, the term "alkoxy," refers to the group —O-alkyl, wherein alkyl is as defined herein. Alkoxy includes, by way of example, methoxy, ethoxy, n-propoxy, isopropoxy, n-butoxy, sec-butoxy, t-butoxy and the like. In an embodiment, $C_1$-$C_3$, $C_1$-$C_4$, $C_1$-$C_6$ alkoxy groups are provided herein.

As used herein, the term "halo" or "halogen" alone or as part of another substituent means, unless otherwise stated, a fluorine, chlorine, bromine, or iodine atom.

As used herein, the term "hydroxyl" refers to the group —OH, wherein the oxygen atom is singly bound to a substituent and a hydrogen atom.

As used herein, the term "cyano" refers to the group —CN, with a single bond between the carbon atom and a substituent and a triple bond between the carbon atom and the nitrogen atom.

As used herein, the term "cycloalkyl" means a non-aromatic carbocyclic system that is partially or fully saturated having 1, 2 or 3 rings wherein such rings may be fused. The term "fused" means that a second ring is present (i.e., attached or formed) by having two adjacent atoms in common (i.e., shared) with the first ring. Cycloalkyl also includes bicyclic structures that may be bridged or spirocyclic in nature with each individual ring within the bicycle varying from 3-10, 3-8, 3-7, 3-6, and 5-10 atoms. The term "cycloalkyl" includes, but is not limited to, cyclopropyl, cyclobutyl, cyclopentyl, cyclohexyl, bicyclo[3.1.0]hexyl, spiro[3.3]heptanyl, bicyclo[2.2.2]octanyl and bicyclo[1.1.1]pentyl. In an embodiment, 3-10 membered cycloalkyl groups are provided herein. In another embodiment, $C_8$ cycloalkyl groups are provided herein. In yet another embodiment, bicyclo-$C_e$ cycloalkyl groups are provided herein. In still another embodiment, bridged-$C_8$ cycloalkyl groups are provided herein.

As used herein, the term "heterocycloalkyl" means a non-aromatic carbocyclic system containing 1, 2, 3 or 4 heteroatoms selected independently from N, O, and S and having 1, 2 or 3 rings wherein such rings may be fused, wherein fused is defined above. Heterocycloalkyl also includes bicyclic structures that may be bridged or spirocyclic in nature with each individual ring within the bicycle varying from 3-8, 5-10, 4-6, or 3-10 atoms, and containing 0, 1, or 2 N, O, or S atoms. The term "heterocycloalkyl" includes cyclic esters (i.e., lactones) and cyclic amides (i.e., lactams) and also specifically includes, but is not limited to, epoxidyl, oxetanyl, tetrahydrofuranyl, tetrahydropyranyl (i.e., oxanyl), pyranyl, dioxanyl, aziridinyl, azetidinyl, pyrrolidinyl, 2,5-dihydro-1H-pyrrolyl, oxazolidinyl, thiazolidinyl, piperidinyl, morpholinyl, piperazinyl, thiomorpholinyl, 1,3-oxazinanyl, 1,3-thiazinanyl, 2-aza-bicyclo[2.1.1]hexanyl, 5-azabicyclo[2.1.1]hexanyl, 6-azabicyclo[3.1.1] heptanyl, 2-azabicyclo-[2.2.1]heptanyl, 3-aza-bicyclo[3.1.1]heptanyl, 2-azabicyclo[3.1.1]heptanyl, 3-azabicyclo-[3.1.0] hexanyl, 2-aza-bicyclo[3.1.0]hexanyl, 3-azabicyclo[3.2.1] octanyl, 8-azabicyclo[3.2.1]-octanyl, 3-oxa-7-aza-bicyclo [3.3.1]nonanyl, 3-oxa-9-azabicyclo[3.3.1]nonanyl, 2-oxa-5-aza-bicyclo[2.2.1]heptanyl, 6-oxa-3-azabicyclo[3.1.1] heptanyl, 2-azaspiro[3.3]heptanyl, 2-oxa-6-azaspiro[3.3] heptanyl, 2-oxaspiro[3.3]heptanyl, 2-oxaspiro[3.5]nonanyl, 3-oxaspiro[5.3]-nonanyl, and 8-oxabicyclo-[3.2.1]octanyl. In an embodiment, 3-10 membered heterocycloalkyl groups are provided herein. In another embodiment, 5-10 membered heterocycloalkyl groups are provided herein. In still another embodiment, 4-6 membered heterocycloalkyl groups are provided herein.

It is to be understood that if a cycloalkyl or heterocycloalkyl moiety may be bonded or otherwise attached to a designated moiety through differing ring atoms (i.e., shown or described without denotation of a specific point of attachment), then all possible points are intended, whether through a carbon atom or, for example, a trivalent nitrogen atom. For example, the term "pyridinyl" means 2-, 3- or 4-pyridinyl, the term "thienyl" means 2- or 3-thioenyl, and so forth.

As used herein, the term "nitro" refers to the group —$NO_2$, wherein the nitrogen atom is singly bound to a substituent, doubly bound to a first oxygen atom, and singly bound to a second oxygen atom. Therefore, the nitrogen atom is positively charged and the second oxygen atom is negatively charged.

As used herein, the term "substituted" means that an atom or group of atoms has replaced hydrogen as the substituent attached to another group.

The compounds provided herein, their syntheses, and their biological activity against ALK2 can be found in PCT/CN2017/093385 (WO2018014829), which is incorporated by reference in its entirety.

Methods of Treatment

In an aspect, provided herein is a method of treating anemia in a subject in need thereof, comprising administering to the subject a compound of Formula I:

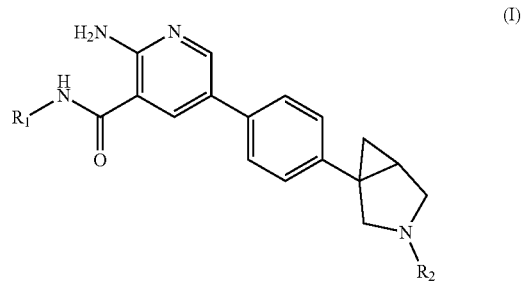

or a pharmaceutically acceptable salt thereof;
wherein
$R_1$ is bridged 5-10 membered cycloalkyl optionally substituted one, two, or three times with hydroxyl or $C_1$-$C_3$ alkoxy;
$R^2$ is selected from the group consisting of $C_1$-$C_3$ alkyl, $C_2$-$C_4$ alkenyl, $C_2$-$C_4$ alkynyl, $C_1$-$C_3$ alkoxy, 3-6 membered cycloalkyl, and 3-6 membered heterocycloalkyl, all of which are optionally substituted with $R^3$; and
$R^3$ is selected from the group consisting of hydroxy, halo, cyano, nitro, $SO_2$—$C_1$-$C_3$ alkyl, and $SO_3H$.

In an embodiment, $R_1$ is bridged C-cycloalkyl substituted with hydroxy.

In another embodiment, $R_2$ is tetrahydropyran.

In yet another embodiment, the compound of Formula I is 2-amino-N-(4-hydroxy-bicyclo[2.2.2]octan-1-yl)-5-(4-(3-(tetrahydro-2H-pyran-4-yl)-3-azabicyclo[3.1.0]hexan-1-yl)phenyl)nicotinamide, or a pharmaceutically acceptable salt thereof.

In still another embodiment, the compound of Formula I is 2-amino-N-(4-hydroxy-bicyclo-[2.2.2]octan-1-yl)-5-(4-((1R,5S)-3-(tetrahydro-2H-pyran-4-yl)-3-azabicyclo[3.1.0] hexan-1-yl)phenyl)nicotinamide, or a pharmaceutically acceptable salt thereof.

In an embodiment, the compound of Formula I is 2-amino-N-(4-hydroxybicyclo[2.2.2]octan-1-yl)-5-(4-((1S, 5R)-3-(tetrahydro-2H-pyran-4-yl)-3-azabicyclo[3.1.0] hexan-1-yl)phenyl)nicotinamide, or a pharmaceutically acceptable salt thereof.

In another embodiment, the compound of Formula I is 2-amino-N-(4-hydroxybicyclo[2.2.2]octan-1-yl)-5-(4-((1R, 5S)-3-(tetrahydro-2H-pyran-4-yl)-3-azabicyclo[3.1.0] hexan-1-yl)phenyl)nicotinamide fumarate dihydrate.

In another embodiment, the subject suffers from a myelodysplastic syndrome (MDS).

In yet another embodiment, the myelodysplastic syndrome (MDS) is selected from the group consisting of MDS with multilineage dysplasia (MDS-MLD), MDS with single lineage dysplasia (MDS-SLD), MDS with excess blasts (MDS-EB), MDS with isolated del(5q), and MDS unclassifiable (MDS-U).

In still another embodiment, the myelodysplastic syndrome (MDS) is MDS with multilineage dysplasia (MDS-MLD). In an embodiment, the myelodysplastic syndrome (MDS) is MDS with single lineage dysplasia (MDS-SLD). In another embodiment, the myelodysplastic syndrome (MDS) is MDS with excess blasts (MDS-EB). In yet another embodiment, the myelodysplastic syndrome (MDS) is MDS with isolated del(5q). In still another embodiment, the myelodysplastic syndrome (MDS) is MDS unclassifiable (MDS-U).

In an embodiment, the subject suffers from multiple myeloma (MM).

In another embodiment, the subject suffers from a myelodysplastic syndrome and myeloproliferative neoplasms (MDS/MPN) overlap syndrome. In yet another embodiment, the MDS/MPN overlap syndrome is chronic myelomonocytic leukemia (CMML) or an unclassifiable MDS/MPN overlap syndrome.

In another embodiment, the subject suffers from myelofibrosis (MF). In yet another embodiment, the anemia is characterized as MF-induced anemia.

In another embodiment, the anemia is iron-refractory iron deficiency anemia (IRIDA).

In yet another embodiment, the subject is transfusion-dependent. In still another embodiment, the subject is not transfusion-dependent.

In an embodiment, the compound of Formula I is administered orally.

In another embodiment, the compound of Formula I is administered as a monotherapy for anemia treatment. In another embodiment, a compound of Formula I is administered as a monotherapy not in conjunction with a Janus kinase inhibitor.

In yet another embodiment, the compound of Formula I is administered at a dose of about 5 mg to about 500 mg once daily (QD). In still another embodiment, the compound of Formula I is administered at a dose of about 50 mg once daily (QD).

In an embodiment, the compound of Formula I is administered at a dose selected from the group consisting of 5 mg, 10 mg, 15 mg, 20 mg, 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, and 500 mg.

In another embodiment, the compound of Formula I is administered at a dose of 5 mg. In yet another embodiment, the compound of Formula I is administered at a dose of 10 mg. In still another embodiment, the compound of Formula I is administered at a dose of 15 mg. In an embodiment, the compound of Formula I is administered at a dose of 20 mg. In another embodiment, the compound of Formula I is administered at a dose of 25 mg. In yet another embodiment, the compound of Formula I is administered at a dose of 50 mg. In another embodiment, the compound of Formula I is administered at a dose of 75 mg. In still another embodiment, the compound of Formula I is administered at a dose of 100 mg. In another embodiment, the compound of Formula I is administered at a dose of 125 mg. In embodiment, the compound of Formula I is administered at a dose of 150 mg. In another embodiment, the compound of Formula I is administered at a dose of 175 mg. In another embodiment, the compound of Formula I is administered at a dose of 200 mg. In another embodiment, the compound of Formula I is administered at a dose of 225 mg. In yet another embodiment, the compound of Formula I is administered at a dose of 250 mg. In another embodiment, the compound of Formula I is administered at a dose of 275 mg. In still another embodiment, the compound of Formula I is administered at a dose of 300 mg. In another embodiment, the compound of Formula I is administered at a dose of 325 mg. In embodiment, the compound of Formula I is administered at a dose of 350 mg. In another embodiment, the compound of Formula I is administered at a dose of 375 mg. In another embodiment, the compound of Formula I is administered at a dose of 400 mg. In another embodiment, the compound of Formula I is administered at a dose of 425 mg. In yet another embodiment, the compound of Formula I is administered at a dose of 450 mg. In another embodiment, the compound of Formula I is administered at a dose of 475 mg. In still another embodiment, the compound of Formula I is administered at a dose of 500 mg.

In an embodiment, the compound of Formula I is orally administered as a tablet. In another embodiment, the compound of Formula I is administered as a 5 mg, 25 mg, or 50 mg tablet, or any combination thereof.

In another aspect, provided herein is a method of treating anemia in a subject in need thereof, comprising administering to the subject 2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide fumarate dihydrate.

In another aspect, provided herein is a method of reducing hepcidin levels in a subject in need thereof, comprising administering to the subject a compound of Formula I:

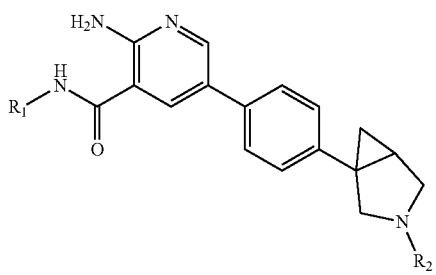

(I)

or a pharmaceutically acceptable salt thereof;
wherein
R₁ is bridged 5-10 membered cycloalkyl optionally substituted one, two, or three times with hydroxyl or $C_1$-$C_3$ alkoxy;
R² is selected from the group consisting of $C_1$-$C_3$ alkyl, $C_2$-$C_4$ alkenyl, $C_2$-$C_4$ alkynyl, $C_1$-$C_3$ alkoxy, 3-6 membered cycloalkyl, and 3-6 membered heterocycloalkyl, all of which are optionally substituted with R³; and
R³ is selected from the group consisting of hydroxy, halo, cyano, nitro, $SO_2$—$C_1$-$C_3$ alkyl, and $SO_3H$.

In an embodiment, R₁ is bridged C-cycloalkyl substituted with hydroxy.

In another embodiment, R₂ is tetrahydropyran.

In yet another embodiment, the compound of Formula I is 2-amino-N-(4-hydroxybicyclo[2.2.2]octan-1-yl)-5-(4-(3-(tetrahydro-2H-pyran-4-yl)-3-azabicyclo[3.1.0]hexan-1-yl)phenyl)nicotinamide, or a pharmaceutically acceptable salt thereof.

In still another embodiment, the compound of Formula I is 2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide, or a pharmaceutically acceptable salt thereof.

In an embodiment, the compound of Formula I is 2-amino-N-(4-hydroxybicyclo[2.2.2]octan-1-yl)-5-(4-((1S,5R)-3-(tetrahydro-2H-pyran-4-yl)-3-azabicyclo[3.1.0]hexan-1-yl)phenyl)nicotinamide, or a pharmaceutically acceptable salt thereof.

In another embodiment, the subject suffers from anemia. In yet another embodiment, the anemia is iron-refractory iron deficiency anemia (IRIDA).

In another embodiment, the subject is transfusion-dependent. In another embodiment, the subject is not transfusion-dependent.

In yet another embodiment, the subject suffers from a myelodysplastic syndrome (MDS).

In another embodiment, the myelodysplastic syndrome (MDS) is selected from the group consisting of MDS with multilineage dysplasia (MDS-MLD), MDS with single lineage dysplasia (MDS-SLD), MDS with excess blasts (MDS-EB), MDS with isolated del(5q), and MDS unclassifiable (MDS-U).

In still another embodiment, the myelodysplastic syndrome (MDS) is MDS with multilineage dysplasia (MDS-MLD). In an embodiment, the myelodysplastic syndrome (MDS) is MDS with single lineage dysplasia (MDS-SLD). In another embodiment, the myelodysplastic syndrome (MDS) is MDS with excess blasts (MDS-EB). In yet another embodiment, the myelodysplastic syndrome (MDS) is MDS with isolated del(5q). In still another embodiment, the myelodysplastic syndrome (MDS) is MDS unclassifiable (MDS-U).

In an embodiment, the subject suffers from multiple myeloma (MM).

In another embodiment, the subject suffers from a myelodysplastic syndrome and myeloproliferative neoplasms (MDS/MPN) overlap syndrome. In yet another embodiment, the MDS/MPN overlap syndrome is chronic myelomonocytic leukemia (CMML) or an unclassifiable MDS/MPN overlap syndrome.

In another embodiment, the subject suffers from myelofibrosis (MF). In yet another embodiment, the anemia is characterized as MF-induced anemia. In still another embodiment, the MF-induced anemia is iron-refractory iron deficiency anemia (IRIDA).

In an embodiment, the compound of Formula I is administered orally.

In another embodiment, the compound of Formula I is administered as a monotherapy to reduce hepcidin levels. In another embodiment, a compound of Formula I is administered as a monotherapy not in conjunction with a Janus kinase inhibitor.

In another aspect, provided herein is a method of treating chronic kidney disease (CDK)-induced anemia in a subject in need thereof, comprising administering to the subject a compound of Formula I:

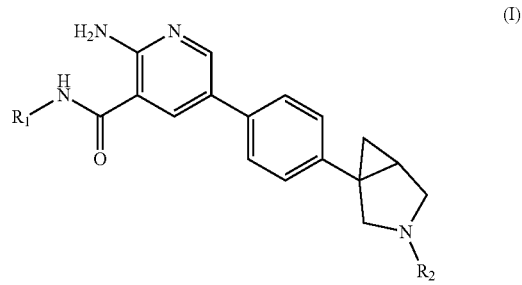

(I)

or a pharmaceutically acceptable salt thereof;
wherein
R₁ is bridged 5-10 membered cycloalkyl optionally substituted one, two, or three times with hydroxyl or $C_1$-$C_3$ alkoxy;
R² is selected from the group consisting of $C_1$-$C_3$ alkyl, $C_2$-$C_4$ alkenyl, $C_2$-$C_4$ alkynyl, $C_1$-$C_3$ alkoxy, 3-6 membered cycloalkyl, and 3-6 membered heterocycloalkyl, all of which are optionally substituted with R³; and
R³ is selected from the group consisting of hydroxy, halo, cyano, nitro, $SO_2$—$C_1$-$C_3$ alkyl, and $SO_3H$.

In an embodiment, the compound of Formula I is 2-amino-N-(4-hydroxybicyclo[2.2.2]octan-1-yl)-5-(4-(3-(tetrahydro-2H-pyran-4-yl)-3-azabicyclo[3.1.0]hexan-1-yl)phenyl)nicotinamide, or a pharmaceutically acceptable salt thereof.

In another embodiment, the compound of Formula I is 2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide, or a pharmaceutically acceptable salt thereof.

In an embodiment, the compound of Formula I is 2-amino-N-(4-hydroxybicyclo[2.2.2]octan-1-yl)-5-(4-((1S,5R)-3-(tetrahydro-2H-pyran-4-yl)-3-azabicyclo[3.1.0]hexan-1-yl)phenyl)nicotinamide, or a pharmaceutically acceptable salt thereof.

In another embodiment, the compound of Formula I is 2-amino-N-(4-hydroxybicyclo[2.2.2]octan-1-yl)-5-(4-((1R, 5S)-3-(tetrahydro-2H-pyran-4-yl)-3-azabicyclo[3.1.0] hexan-1-yl)phenyl)nicotinamide fumarate dihydrate.

In yet another embodiment, the compound of Formula I is administered as a monotherapy to treat chronic kidney disease (CDK)-induced anemia.

In another aspect, provided herein is a method of treating anemia in a subject in need thereof, comprising administering to the subject a compound of Formula I:

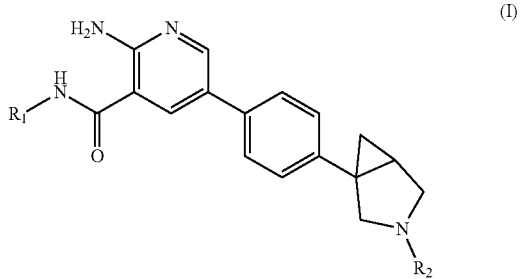

(I)

or a pharmaceutically acceptable salt thereof;
wherein
$R_1$ is bridged 5-10 membered cycloalkyl optionally substituted one, two, or three times with hydroxyl or $C_1$-$C_3$ alkoxy;
$R^2$ is selected from the group consisting of $C_1$-$C_3$ alkyl, $C_2$-$C_4$ alkenyl, $C_2$-$C_4$ alkynyl, $C_1$-$C_3$ alkoxy, 3-6 membered cycloalkyl, and 3-6 membered heterocycloalkyl, all of which are optionally substituted with $R^3$; and
$R^3$ is selected from the group consisting of hydroxy, halo, cyano, nitro, $SO_2$—$C_1$-$C_3$ alkyl, and $SO_3H$;
wherein the subject suffers from myelofibrosis (MF) and was previously treated with a JAK inhibitor or is not eligible to receive a JAK inhibitor treatment.

In an embodiment, the subject was previously treated with a JAK inhibitor. In another embodiment, the subject is not eligible to receive a JAK inhibitor treatment. In yet another embodiment, the subject is not eligible to receive a JAK inhibitor treatment because the subject is intolerant to the JAK inhibitor treatment.

In an embodiment, $R_1$ is bridged $C_8$-cycloalkyl substituted with hydroxy.

In another embodiment, $R_2$ is tetrahydropyran.

In yet another embodiment, the compound of Formula I is 2-amino-N-(4-hydroxybicyclo[2.2.2]octan-1-yl)-5-(4-(3-(tetrahydro-2H-pyran-4-yl)-3-azabicyclo[3.1.0]hexan-1-yl) phenyl)nicotinamide, or a pharmaceutically acceptable salt thereof.

In still another embodiment, the compound of Formula I is 2-amino-N-(4-hydroxybicyclo[2.2.2]octan-1-yl)-5-(4-((1R,5S)-3-(tetrahydro-2H-pyran-4-yl)-3-azabicyclo[3.1.0] hexan-1-yl)phenyl)nicotinamide, or a pharmaceutically acceptable salt thereof.

In an embodiment, the compound of Formula I is 2-amino-N-(4-hydroxybicyclo[2.2.2]octan-1-yl)-5-(4-((1S, 5R)-3-(tetrahydro-2H-pyran-4-yl)-3-azabicyclo[3.1.0] hexan-1-yl)phenyl)nicotinamide, or a pharmaceutically acceptable salt thereof.

In an embodiment of the methods, the compound of Formula I is administered at a dose of about 5 mg to about 500 mg once daily (QD). In still another embodiment, the compound of Formula I is administered at a dose of about 50 mg once daily (QD).

In an embodiment, the compound of Formula I is administered at a dose selected from the group consisting of 5 mg, 10 mg, 15 mg, 20 mg, 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, and 500 mg.

In another embodiment, the compound of Formula I is administered at a dose of 5 mg. In yet another embodiment, the compound of Formula I is administered at a dose of 10 mg. In still another embodiment, the compound of Formula I is administered at a dose of 15 mg. In an embodiment, the compound of Formula I is administered at a dose of 20 mg. In another embodiment, the compound of Formula I is administered at a dose of 25 mg. In yet another embodiment, the compound of Formula I is administered at a dose of 50 mg. In another embodiment, the compound of Formula I is administered at a dose of 75 mg. In still another embodiment, the compound of Formula I is administered at a dose of 100 mg. In another embodiment, the compound of Formula I is administered at a dose of 125 mg. In embodiment, the compound of Formula I is administered at a dose of 150 mg. In another embodiment, the compound of Formula I is administered at a dose of 175 mg. In another embodiment, the compound of Formula I is administered at a dose of 200 mg. In another embodiment, the compound of Formula I is administered at a dose of 225 mg. In yet another embodiment, the compound of Formula I is administered at a dose of 250 mg. In another embodiment, the compound of Formula I is administered at a dose of 275 mg. In still another embodiment, the compound of Formula I is administered at a dose of 300 mg. In another embodiment, the compound of Formula I is administered at a dose of 325 mg. In embodiment, the compound of Formula I is administered at a dose of 350 mg. In another embodiment, the compound of Formula I is administered at a dose of 375 mg. In another embodiment, the compound of Formula I is administered at a dose of 400 mg. In another embodiment, the compound of Formula I is administered at a dose of 425 mg. In yet another embodiment, the compound of Formula I is administered at a dose of 450 mg. In another embodiment, the compound of Formula I is administered at a dose of 475 mg. In still another embodiment, the compound of Formula I is administered at a dose of 500 mg.

In an embodiment, the compound of Formula I is orally administered as a tablet. In another embodiment, the compound of Formula I is administered as a 5 mg, 25 mg, or 50 mg tablet, or any combination thereof.

In yet another aspect, provided herein is a method of reducing hepcidin levels in a subject in need thereof, comprising administering to the subject 2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl) phenyl)nicotinamide fumarate dihydrate.

In an aspect, provided herein is a method of treating myelodysplastic syndrome (MDS) in a subject in need thereof, comprising administering to the subject a compound of Formula I:

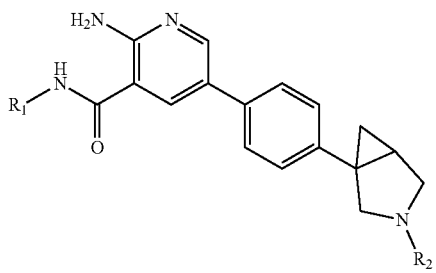

(I)

or a pharmaceutically acceptable salt thereof;
wherein
$R_1$ is bridged 5-10 membered cycloalkyl optionally substituted one, two, or three times with hydroxyl or $C_1$-$C_3$ alkoxy;
$R_2$ is selected from the group consisting of $C_1$-$C_3$ alkyl, $C_2$-$C_4$ alkenyl, $C_2$-$C_4$ alkynyl, $C_1$-$C_3$ alkoxy, 3-6 membered cycloalkyl, and 3-6 membered heterocycloalkyl, all of which are optionally substituted with $R^3$; and
$R^3$ is selected from the group consisting of hydroxy, halo, cyano, nitro, $SO_2$—$C_1$-$C_3$ alkyl, and $SO_3H$.

In yet another embodiment, the compound of Formula I is 2-amino-N-(4-hydroxybicyclo[2.2.2]octan-1-yl)-5-(4-(3-(tetrahydro-2H-pyran-4-yl)-3-azabicyclo[3.1.0]hexan-1-yl)phenyl)nicotinamide, or a pharmaceutically acceptable salt thereof.

In still another embodiment, the compound of Formula I is 2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide, or a pharmaceutically acceptable salt thereof.

In an embodiment, the compound of Formula I is 2-amino-N-(4-hydroxybicyclo[2.2.2]octan-1-yl)-5-(4-((1S,5R)-3-(tetrahydro-2H-pyran-4-yl)-3-azabicyclo[3.1.0]hexan-1-yl)phenyl)nicotinamide, or a pharmaceutically acceptable salt thereof.

In another embodiment, the compound of Formula I is 2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide fumarate dihydrate.

In another aspect, provided herein is a method of treating multiple myeloma (MM) in a subject in need thereof, comprising administering to the subject a compound of Formula I:

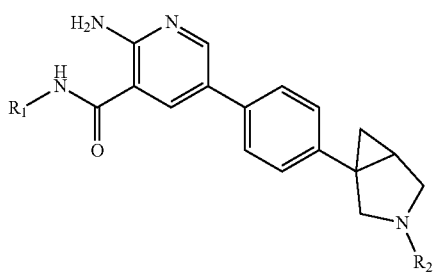

(I)

or a pharmaceutically acceptable salt thereof;
wherein
$R_1$ is bridged 5-10 membered cycloalkyl optionally substituted one, two, or three times with hydroxyl or $C_1$-$C_3$ alkoxy;
$R^2$ is selected from the group consisting of $C_1$-$C_3$ alkyl, $C_2$-$C_4$ alkenyl, $C_2$-$C_4$ alkynyl, $C_1$-$C_3$ alkoxy, 3-6 membered cycloalkyl, and 3-6 membered heterocycloalkyl, all of which are optionally substituted with $R^3$; and
$R^3$ is selected from the group consisting of hydroxy, halo, cyano, nitro, $SO_2$—$C_1$-$C_3$ alkyl, and $SO_3H$.

In yet another embodiment, the compound of Formula I is 2-amino-N-(4-hydroxybicyclo[2.2.2]octan-1-yl)-5-(4-(3-(tetrahydro-2H-pyran-4-yl)-3-azabicyclo[3.1.0]hexan-1-yl)phenyl)nicotinamide, or a pharmaceutically acceptable salt thereof.

In still another embodiment, the compound of Formula I is 2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide, or a pharmaceutically acceptable salt thereof.

In an embodiment, the compound of Formula I is 2-amino-N-(4-hydroxybicyclo[2.2.2]octan-1-yl)-5-(4-((1S,5R)-3-(tetrahydro-2H-pyran-4-yl)-3-azabicyclo[3.1.0]hexan-1-yl)phenyl)nicotinamide, or a pharmaceutically acceptable salt thereof.

In another embodiment, the compound of Formula I is 2-amino-N-(4-hydroxybicyclo[2.2.2]octan-1-yl)-5-(4-((1R,5S)-3-(tetrahydro-2H-pyran-4-yl)-3-azabicyclo[3.1.0]hexan-1-yl)phenyl)nicotinamide fumarate dihydrate.

In another embodiment of the methods, the subject is human.

In some embodiments, the method or treatment reduces hepcidin serum levels in patients relative to baseline or compared to levels in healthy individuals. The hepcidin serum levels can be reduced by more than about 5%, 10%, 20%, 30%, 40%, 50%, 60%, 70%, 80%, 90% or about 100%. In some embodiments, the hepcidin serum levels are reduced by about 50% or more relative to baseline. In some embodiments, the hepcidin serum levels are reduced to less than about 150 ng/mL, 140, 130, 120, 110, 100, 90, 80, 70, 60 or about 50 ng/mL. Hepcidin levels can be tested by standard techniques, including radioimmunoassays, ELISA, ligand binding assay or mass spectrometry.

In some embodiments, the method or treatment increases serum iron concentration in patients relative to baseline or compared to levels in healthy individuals. The serum iron concentration can be increased by more than about 5%, 10%, 20%, 30%, 40%, 50%, 60%, 70%, 80%, 90% or about 100%. Serum iron concentration can be tested by standard techniques.

In some embodiments, the method or treatment increases hemoglobin serum levels in patients relative to baseline or compared to levels in healthy individuals. The hemoglobin serum levels can be increased by more than about 5%, 10%, 15%, 20%, 25% or about 30%. Hemoglobin levels can be tested by standard techniques.

In some embodiments, the method or treatment increases transferrin saturation (TSAT) in patients relative to baseline or compared to levels in healthy individuals. The TSAT can be increased by more than about 5%, 10%, 15%, 20%, 25% or about 30%. TSAT can be tested by standard techniques.

In some embodiments, the method or treatment reduces ferritin blood levels in patients relative to baseline or compared to levels in healthy individuals. The ferritin blood levels can be reduced by more than about 5%, 10%, 20%, 30%, 40%, 50%, 60%, 70%, 80%, 90% or about 100%. Ferritin blood levels can be tested by standard techniques.

Administration/Dosage/Formulations

In another aspect, provided herein is a pharmaceutical composition or pharmaceutical combination comprising the compounds disclosed herein, together with a pharmaceutically acceptable carrier.

Administration of the combination includes administration of the combination in a single formulation or unit dosage form, administration of the individual agents of the combination concurrently but separately, or administration of the individual agents of the combination sequentially by any suitable route. The dosage of the individual agents of the combination may require more frequent administration of one of the agent(s) as compared to the other agent(s) in the combination. Therefore, to permit appropriate dosing, packaged pharmaceutical products may contain one or more dosage forms that contain the combination of agents, and one or more dosage forms that contain one of the combination of agents, but not the other agent(s) of the combination.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could begin administration of the pharmaceutical composition to dose the disclosed compound at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of the disclosed compound calculated to produce the desired therapeutic effect in association with the required pharmaceutical vehicle. The dosage unit forms are dictated by and directly dependent on (a) the unique characteristics of the disclosed compound and the particular therapeutic effect to be achieved, and (b) the limitations inherent in the art of compounding/formulating such a disclosed compound for the treatment of pain, a depressive disorder, or drug addiction in a patient.

In one embodiment, the compounds provided herein are formulated using one or more pharmaceutically acceptable excipients or carriers. In one embodiment, the pharmaceutical compositions provided herein comprise a therapeutically effective amount of a disclosed compound and a pharmaceutically acceptable carrier.

Routes of administration of any of the compositions discussed herein include oral, nasal, rectal, intravaginal, parenteral, buccal, sublingual or topical. The compounds may be formulated for administration by any suitable route, such as for oral or parenteral, for example, transdermal, transmucosal (e.g., sublingual, lingual, (trans)buccal, (trans) urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration. In one embodiment, the preferred route of administration is oral.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions are not limited to the particular formulations and compositions that are described herein.

For oral application, particularly suitable are tablets, dragees, liquids, drops, suppositories, or capsules, caplets and gel caps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For parenteral administration, the disclosed compounds may be formulated for injection or infusion, for example, intravenous, intramuscular or subcutaneous injection or infusion, or for administration in a bolus dose or continuous infusion. Suspensions, solutions or emulsions in an oily or aqueous vehicle, optionally containing other formulatory agents such as suspending, stabilizing or dispersing agents may be used.

Kits

The present disclosure also includes pharmaceutical kits useful, e.g., in the treatment or prevention of diseases or disorders associated with the activity of ALK2, such as anemia, which include one or more containers containing a pharmaceutical composition comprising a therapeutically effective amount of a compound of Formula I, or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

Those skilled in the art will recognize, or be able to ascertain using no more than routine experimentation, numerous equivalents to the specific procedures, embodiments, claims, and examples described herein. Such equivalents were considered to be within the scope of this disclosure and covered by the claims appended hereto. For example, it should be understood that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present application.

The following examples further illustrate aspects of the present disclosure. However, they are in no way a limitation of the teachings of the present disclosure as set forth.

EXAMPLES

The compounds and methods disclosed herein are further illustrated by the following examples, which should not be construed as further limiting. The practice of the present disclosure will employ, unless otherwise indicated, conventional techniques of organic synthesis, cell biology, cell culture, and molecular biology, which are within the skill of the art.

Processes for preparing the compounds disclosed herein can be found, at least, in WO 2018/014829, the content of which is hereby incorporated in its entirety.

Example 1: Clinical Protocol

A Phase 1a, double-blind, randomized, placebo-controlled, single-dose, dose-escalation and food-effect study is being conducted with 2-amino-N-(4-hydroxybicyclo-[2.2.2]octan-1-yl)-5-(4-((1R,5S)-3-(tetrahydro-2H-pyran-4-yl)-3-azabicyclo-[3.1.0]hexan-1-yl)phenyl)nicotinamide ("Compound A") in order to assess the safety, tolerability, and pharmacokinetics (PK) of Compound A when administered orally as a single dose to healthy adult participants.

Compound A has been administered as a single dose at the dose levels of 10 mg, 25 mg, 50 mg, 100 mg, and 175 mg once to 9 healthy participants at each dose level. No severe adverse events (SAEs) have been observed and all adverse events (AEs) were mild and self-limiting for all dose levels.

1.1. Benefit/Risk Assessment

The study design will maximize participant safety while important PK information is collected. Dose escalation will proceed with safety information and PK data collected as the study progresses. All AEs (including hematology, blood chemistry, and liver function test abnormalities) will be monitored in all participants to identify occurrences of any safety signal.

In the 28-day repeat dose toxicity studies of Compound A in rats and dogs, findings at the no observed adverse effect level (NOAEL) in both species were limited to slight increases in iron staining in the liver with no associated increase in liver function tests (LFTs) or microscopic findings in the liver; these findings were attributed to ALK2-mediated alterations in iron metabolism. At higher doses, increases in serum alanine aminotransferase (ALT) and aspartate aminotransferase (AST) and microscopic findings in the liver were observed that were considered secondary to liver iron accumulation. Iron parameters and liver functional tests will be monitored clinically.

Additional adverse findings considered to be related to the inhibition of ALK3 at higher doses included mucosal hypertrophy and hyperplasia in the gastrointestinal tract with associated changes in the mesenteric lymph nodes, anagen phase arrest of hair follicles, and further alterations in iron metabolism. Additionally, increased heart rates were observed in dogs at higher doses. Potential increases in heart rate, skin/hair, and the gastrointestinal track will also be monitored clinically.

All adverse findings in nonclinical toxicology studies were associated with exposures that exceed the anticipated exposures in participants over the planned dose range.

1.2. Details of Objectives and Endpoints

Table 1 presents the study objectives and endpoints.

TABLE 1

| Objectives | Endpoints |
|---|---|
| \multicolumn{2}{c}{Primary} | |
| To determine the safety and tolerability of Compound A in MDS and MM participants | Frequency and severity of AEs and SAEs, including changes in vital signs, ECGs, physical examinations, and clinical blood and urine laboratory parameters. Identification of the DLTs, MTD, and RDE. |
| \multicolumn{2}{c}{Secondary} | |
| To determine the efficacy of Compound A in MDS and MM participants | For both MDS and MM disease groups: For transfusion independent (TI) participants at baseline: Anemia response defined as an Hgb increase of at least 1.5 g/dL relative to baseline for any 8-week period (with each assessment meeting this requirement) during the first 24 weeks of treatment. Duration of the anemia response defined as the interval from the first onset of anemia response to the earliest date of loss of anemia response that persists for at least 4 weeks or death from any cause. For transfusion-dependent (TD) participants at baseline: Red blood cell-transfusion independency (RBC-TI) defined as the absence of any RBC-transfusion for at least 8 consecutive weeks during the first 24 weeks of treatment. Duration of RBC-TI period for participants achieving RBC-TI for at least 8 consecutive weeks during the first 24 weeks of treatment. |

TABLE 1-continued

Objectives and Endpoints

| Objectives | Endpoints |
|---|---|
| | Rate of RBC transfusion through Weeks 12 and 24, defined as the average number of RBC units per participant-month during the treatment period. The largest increase from baseline in the mean Hgb values over any rolling 8-week treatment period during the first 24 weeks of treatment. For MDS participants only: Overall response defined as the proportion of participants with CR or PR as per Cheson et al 2006 definitions for MDS and as per Savona et al 2015 definitions for MDS/MPN overlap syndromes, as applicable. Progression-free survival (PFS) defined as the interval from the first dose of study drug until the first documented progression or death as per Cheson et al 2006 definitions for MDS and to Savona et al 2015 definitions for MDS/MPN overlap syndromes. Leukemia-free survival (LFS) defined as the interval from the first dose of study drug until the first documented leukemia transformation or death from any cause. For MM participants only: Overall response rate defined as the proportion of participants with stringent complete response, complete response, very good partial response, and partial response as per Kumar S, et al. *Lancet Oncol* 2016;17:e328-46. Progression-free survival (PFS) defined as the interval from the first dose of study drug until the first documented progression or death as per Kumar et al 2016. |
| To evaluate the PK of Compound A in MDS and MM participants | Pharmacokinetics (PK) parameters: $C_{max}$, $T_{max}$ and $AUC_{0-t}$. |
| To evaluate the effect of Compound A on the iron homeostasis and the erythro-poiesis in MDS and MM participants. | Blood samples will be drawn to assess the: defined as the absence of any RBC-transfusion for at Blood levels of hepcidin, Iron homeostasis parameters, Erythropoiesis parameters |

ECG = electrocardiogram; DLT = dose-limiting toxicity; MTD = maximum tolerated dose; RDE = recommended dose for expansion; Hgb = hemoglobin; TI = transfusion independent; CR = complete response; PR = partial response 2. Study Design
2.1. Overall Design This Phase ½, open-label, multicenter, dose-finding study is intended to evaluate the safety and tolerability, PK, PD, and preliminary efficacy of Compound A administered as monotherapy in participants with MDS or MM who are transfusion-dependent or presenting with symptomatic anemia.

2.2. Overall Study Duration

The study begins when the first participant signs the informed consent form (ICF). The end of the study will occur when all participants have completed up to 6 months of treatment or have discontinued treatment earlier and completed applicable safety follow-up assessments or when the sponsor terminates the study. The participants who are still receiving Compound A, who are deriving clinical benefit, and who do not have any evidence of progressive disease at time of study closure may have the option to continue receiving treatment with Compound A under this trial or a roll-over protocol.

A participant is considered to have completed the study if he/she has completed all stages of the study including the safety follow-up visit. For each participant, the study will comprise the following:
  Up to 28 days for screening.
  Continuous study drug treatment in consecutive 28-day treatment cycles up to 6 months as long as participants are deriving benefit from study drug and have not met any criteria for study drug discontinuation.
  An additional 30 days for the safety follow-up period.
  Post-treatment follow-up every 6 months.

2.3. Study Termination

The investigator retains the right to terminate study participation at any time, according to the terms specified in the study contract. The investigator is to notify the institutional review board/independent ethics committee (IRB/IEC) of the study's completion or early termination, send a copy of the notification to the sponsor or sponsor's designee, and retain 1 copy for the site study regulatory file.

The sponsor may terminate the study electively, if required by regulatory decision, or upon advice of the data monitoring committee (DMC). If the study is terminated prematurely, the sponsor will notify the investigators, the IRBs/IECs, and regulatory bodies of the decision and reason for termination of the study. The DMC may recommend termination of the study if warranted.

3. Study Population

Deviations from eligibility criteria are not allowed because they can potentially jeopardize the scientific integrity of the study, regulatory acceptability, and/or participant safety. Therefore, adherence to the criteria as specified in the Protocol is essential. Prospective approval of Protocol deviations to recruitment and enrollment criteria, also known as Protocol waivers or exemptions, are not permitted.

3.1. Inclusion Criteria

Participants are eligible to be included in the study only if all of the following criteria apply:

1. Ability to comprehend and willingness to sign a written informed consent form (ICF) for the study.
2. Age 18 years or older at the time of signing the ICF.
3. Eastern Cooperative Oncology Group (ECOG) performance status score of the following:
    a. 0 or 1 for the dose-escalation stages.
    b. 0, 1, or 2 for the dose-expansion stage.
4. Life expectancy is greater than 6 months.
5. Agreement to avoid pregnancy or fathering children based on the criteria below:
    a. Male participants with reproductive potential must agree to take appropriate precautions to avoid fathering children from screening through 90 days after the last study drug dose and must refrain from donating sperm during this period. Permitted methods in preventing pregnancy should be communicated to the participants and their understanding confirmed.
    b. Female participants who are women of childbearing potential (WOCBP) must have a negative serum pregnancy test at screening before the first dose (within 3 days of the first study drug dose) and must agree to take appropriate precautions to avoid pregnancy from screening through the safety follow-up visit (see Table 2). Permitted methods in preventing pregnancy should be communicated to the participants and their understanding confirmed,
    c. Female participants not considered to be of childbearing are eligible.

TABLE 2

| | Scr. | Treatment period | | | | | | | | | |
| --- | --- | --- | --- | --- | --- | --- | --- | --- | --- | --- | --- |
| | D-28 | Cycle 1 | | | | Cycle 2 | | ≥Cycle 3 | | | |
| | to | Day | Day | Day | Day | Day | Day | Day | Day | Follow-up | |
| | D0 | 1 | 8 | 15 | 22 | 1 | 15 | 1 | 15 | EOT | Safety | Post-treat. |
| Laboratory Assessments | | | | | | | | | | | |
| Pregnancy testing | X | | | | | X | | X | | X | X |
| Hematology | X | X | X | X | X | X | | X | | X | X |
| Hemoglobin only | | | | | | | X | | X | | |
| Serum chemistry | X | X | X | X | | X | | X | | X | X |
| HbA1c, Vitamin B12 and MMA | X | | | | | | | Q. 3 cycles (Day 1) | | X | |
| Serology screening | X | | | | | | | | | | |
| Lipid panel | X | X | | | | X | | X | | X | X |
| Coagulation panel | X | X | | | | X | | C3D1 only | | X | X |
| Urinalysis | X | | | | | | | | | X | |
| PK Sampling Schedule | | | | | | | | | | | |
| Blood PK sample | | X | | X | | | | | | | |
| PD Sampling Schedule | | | | | | | | | | | |
| Plasma PD | | X | X | X | | X | | X | | | |
| Iron metabolism, erythropoiesis parameters and EPO | X | X | X | X | | X | | X | | X | X |
| Plasma correlative (pre dose) | | X | | | | X | | C4D1 only | | | |
| BM smear* | | X | | | | | | | | | |
| Post-Treatment Assessments | | | | | | | | | | | |
| Leukemia progression/ Disease progression/ New anti-cancer treatment | | | | | | | | | | | | X |

C3D1—cycle 3, day 1; C4D1—cycle 4, day 1; wherein 1 cycle is 28 days.

Inclusion Criteria Defining the Disease Characteristics:
  6. Participants who are transfusion-dependent or present with symptomatic anemia, defined as follows:
    a. Anemia: An Hgb value <10 g/dL demonstrated during screening recorded on 3 separate occasions with at least 7 days between measurements (Note: RBC transfusion must be at least 2 weeks before the Hgb measurement during screening).
    b. Transfusion-dependent: Participant has received at least 4 units of RBC transfusions during the 28 days immediately preceding Cycle 1 Day 1 OR has received at least 4 units of RBC transfusions in the 8 weeks immediately preceding Cycle 1 Day 1, for an Hgb level of <8.5 g/dL, in the absence of bleeding or treatment-induced anemia. In addition, the most recent transfusion episode must have occurred in the 28 days before Cycle 1 Day 1.
For MDS Participants:
  7. Ineligible to receive or have not responded to available therapies for anemia such as ESAs or lenalidomide.
  8. Participants not requiring cytoreductive therapy other than hydroxyurea.
  9. Participants with BM and peripheral blood myeloblast count <10%.
  10. Histologically confirmed diagnosis of the following (according to the 2016 WHO criteria [Swerdlow et al 2017]):
    a. MDS.
    b. CMML.
    c. Unclassifiable MDS/MPN overlap syndrome.
  Note: Participants presenting with MDS-RS or with atypical chronic myeloid leukemia, juvenile myelomonocytic leukemia, or MDS/MPN with ring sideroblasts and thrombocytosis will not be included.
For MM Participants:
  11. Histologically confirmed diagnosis of multiple myeloma (according to the 2016 WHO criteria [Swerdlow et al 2017]):
  12. After failure of available standard treatments; standard treatment options include the following: alkylating agent, glucocorticoids, immunomodulatory drugs IMiD (lenalidomide, pomalidomide or thalidomide), proteasome inhibitors (bortezomib or carfilzomib), and daratumumab.

3.2. Exclusion Criteria

Participants are excluded from the study if any of the following criteria apply:
  1. Undergone any prior allogenic stem cell transplantation or a candidate for such transplantation.
  2. Any major surgery within 28 days before the first dose of study drug.
  3. Any prior chemotherapy, immunomodulatory drug therapy, immunosuppressive therapy, biological therapy, endocrine therapy, targeted therapy, antibody or hypomethylating agent to treat the participant's disease, within 5 half-lives or 28 days (whichever is shorter) before the first dose of study drug.
    a. Except glucocorticoids (steroids may be continued during study if the participant had a stable dose for the 4 weeks immediately prior C1D1 and does not present any Grade 2 or higher toxicity due to the treatment) and hydroxyurea (may be sued to treat hyperproliferative disease from Cycle 2 in dose escalation cohorts and from Cycle 1 in dose expansion) allowed.
  4. Undergoing treatment with another investigational medication or having been treated with an investigational medication within 28 days before the first dose of study drug. Note: The Sponsor's medical monitor should be contacted in the event a participant had to receive any treatment to treat COVID-19 signs or symptoms.
  5. Participants undergoing treatment with ESAs, G-CSF or GM-CSF, romiplostin, or eltrombopag at any time within 28 days before the first dose of study drug.
  6. Undergoing treatment with a potent/strong inhibitor or inducer of CYP3A4/5 within 28 days or 5 half-lives (whichever is longer) before the first dose of study drug, or expected to receive such treatment during the study.
  7. Any prior radiation therapy within 28 days before the first dose of study drug. Palliative radiation therapy to single sites or small fields is allowed with at least a 1-week washout before the first dose of study drug.
  8. Presence of any hematological malignancy other than MDS or MM, as applicable.
  9. Active invasive malignancy over the previous 5 years. Exceptions include participants with early-stage basal cell or squamous cell skin cancer, completely resected intraepithelial carcinoma of the cervix, or completely resected papillary thyroid and follicular thyroid cancers, who may be eligible to participate at the investigator's discretion. Participants with malignancies with indolent behavior such as prostate cancer treated with radiation or surgery may be enrolled as long as they have a reasonable expectation to have been cured with the treatment modality received.
  10. Known active disease involving the CNS.
  11. History of clinically significant or uncontrolled cardiac disease, including recent (within the last 12 months) unstable angina or acute myocardial infarction, or New York Heart Association Class Ill or IV congestive heart failure, or clinically significant arrhythmias not controlled by medication. Participants with a pacemaker and well-controlled rhythm for at least 1 month before the first dose of study medication will be allowed.
  12. History or presence of an abnormal ECG that, in the investigator's opinion, is clinically meaningful. Screening QTc interval >450 milliseconds is excluded unless approved by the sponsor's medical monitor. For participants with an intraventricular conduction delay (QRS interval 120 milliseconds), the JTc interval may be used in place of the QTc with sponsor approval. Participants with left bundle branch block are excluded. Participants with QTc prolongation due to a pacemaker may enroll with prior approval from the sponsor's medical monitor.
  13. Presence of chronic or current active infectious disease requiring systemic antibiotic, antifungal, or antiviral treatment. Participants with acute infection requiring antibiotic, antifungal, or antiviral treatment use should delay screening/enrollment until the course of antibiotic antifungal, or antiviral therapy has been completed and the infection is not active anymore.
  14. Participants with diagnosis of chronic liver disease (e.g., chronic alcoholic liver disease, autoimmune hepatitis, sclerosing cholangitis, primary biliary cirrhosis, hemochromatosis, nonalcoholic steatohepatitis).
  15. Participants with known active hepatitis A, HBV, or HCV infection or who are known to be HIV-positive.
  16. Unwillingness to be transfused with blood components including RBC packs and platelet transfusions.

17. Any condition in the investigator's judgment that would interfere with full participation in the study (e.g., unable, unlikely, or unwilling to comply with the dose schedule and study evaluations), including administration of study drug and attending required study visits; pose a significant risk to the participant; or interfere with interpretation of study data.
18. Active alcohol or drug addiction that would interfere with their ability to comply with the study requirements.
19. Gastroesophageal reflux disease not controlled by medication (i.e., currently symptomatic or endoscopic evidence of esophagitis) within 28 days before the first dose of study drug.
20. Has any unresolved toxicity Grade 2 from previous therapy except for stable chronic toxicities (s Grade 2) not expected to resolve, such as stable Grade 2 peripheral neuropathy.
21. Known hypersensitivity, severe reaction, or any known contraindications to the use of any of the active substances or excipients in a pharmaceutical composition comprising Compound A.
22. Women who are pregnant or breastfeeding.
23. Unable to swallow and retain oral medication.
24. Current use of prohibited medication.
25. Participants with laboratory values at screening as defined in Table 3.

Example 2: Clinical Protocol for MF-Induced Anemia

This study is a phase ½, open-label, multicenter, dose-escalation and -expansion study assessing Compound A alone (treatment group A [TGA]) or in combination with ruxolitinib (treatment group B [TGB]), in patients with MF who are transfusion-dependent or present with symptomatic anemia. For TGA, must be either previously treated with JAK inhibitors (for at least 12 weeks and are resistant, refractory, or lost response to a JAK inhibitor), or are intolerant, or are not eligible to receive a JAK inhibitor treatment (e.g., participants who did not receive any JAK inhibitor treatment due to severe anemia and/or without any symptoms except ones due to anemia and without splenomegaly) and have a risk category of intermediate-2 or high according to the Dynamic International Prognostic Scoring System (DIPSS); for TGB, patients must have been on a therapeutic and stable regimen of ruxolitinib for 12 consecutive weeks prior to first dose of study treatment and have a DIPSS risk category of intermediate-1 or -2, or high. To be eligible patients must be ≥18 years of age, have an Eastern Cooperative Oncology Group (ECOG) performance status 0-1 for the dose-escalation stages or 0-2 for the dose-expansion stage, have life expectancy >6 months, and have histologically confirmed primary or secondary (post-polycythemia vera, post-essential thrombocythemia) MF.

TABLE 3

Exclusionary Laboratory Values

| | Laboratory Parameter | Exclusion Criterion |
|---|---|---|
| | | Hematology |
| a | Platelets | $<50 \times 10^9$/L without the assistance of growth factors, thrombopoietic factors, or platelet transfusions |
| b | ANC | $<0.75 \times 10^9$/L |
| | | Hepatic |
| c | ALT | ≥2.5 × ULN |
| d | AST | ≥2.5 × ULN |
| e | Total bilirubin | ≥2.0 ULN, unless conjugated (direct) bilirubin is ≤1.5 ULN (direct bilirubin only needs to be tested if total bilirubin exceeds the ULN; except known Gilbert's syndrome, in which case direct bilirubin has to be tested). If there is no institutional ULN, then direct bilirubin must be <40% of total bilirubin |
| f | ALP | ≥3 × ULN |
| | | Renal |
| g | Creatinine clearance | <30 mL/min according to Cockcroft-Gault formula. |
| | | Others |
| h | Iron metabolism | Serum ferritin level > 1000 ng/ml and documented clinically significant iron overload on liver MRI or biopsy. |

ANC = absolute neutrophil count; ALP = alkaline phosphatase; ULN = upper limit of normal Primary Analysis and Study Closure The primary analysis will be conducted after all participants have completed at least 6 months of study drug treatment and have completed all safety assessments at Cycle 6 or have discontinued study drug earlier. The participants who are still receiving Compound A, who are deriving clinical benefit, and who do not have any evidence of progressive disease at time of study closure may have the option to continue receiving treatment with Compound A. The end of the study will occur when all participants have discontinued treatment and completed applicable safety follow-up assessments or when the sponsor terminates the study.

Patients are ineligible if they have any other hematologic malignancy; have undergone any prior allogeneic or autologous stem cell transplantation; have undergone major surgery within 28 days of first dose of study drug; or received prior chemotherapy, immunomodulatory drug, immunosuppressive, biological, endocrine, or targeted therapy, or an antibody/hypomethylating agent within 5 half-lives or 28 days before first dose of study drug.

In Part 1 (dose escalation) of the study, patients will be enrolled into TGA or TGB. Compound A monotherapy will be administered orally at a starting dose of 50 mg/day in TGA (28-day cycles). Dose-escalation stages will use a Bayesian optimal interval design to determine the maximum tolerated dose (MTD), with dose increases not exceeding 100% (2-fold) until a treatment-related toxicity Grade ≥2 is observed. Dose escalation in TGB will start 2 dose levels below the maximum evaluated dose determined to be safe and tolerable in TGA (recommended dose expansion [RDE]); patients in TGB will receive Compound A in combination with ruxolitinib. In each treatment group in Part 1, ≤24 patients will be treated in the dose-escalation stage. In Part 2 (dose expansion), the RDE in TGB will be evaluated in combination with ruxolitinib in approximately 25 patients. Patients will receive treatment for up to 12 months, and treatment may continue if patients are deriving clinical benefit and have no evidence of progressive disease.

The primary study objective is to determine the safety and tolerability of Compound A monotherapy or in combination with ruxolitinib (assessed by the frequency and severity of adverse events [AEs], physical examinations, and monitoring vital signs and laboratory values, and identification of dose-limiting toxicities, MTD, and RDE for TGB). Secondary objectives are to determine the efficacy of Compound A monotherapy or in combination with ruxolitinib (assessed by anemia response, duration of anemia response, mean change from baseline in hemoglobin, and rate of RBC transfusion through week 24 and 48), evaluate pharmacokinetics of Compound A, and evaluate the effect of Compound A as monotherapy or in combination with ruxolitinib on hepcidin level, iron homeostasis, and erythropoiesis.

Example 3: Mouse Adenine-Induced Chronic Kidney Disease Model

The anemia associated with chronic kidney disease has been associated with the hepatic hormone hepcidin (Akchurin et al., Am. J. Physiol. Renal Physiol., 2016). Therefore, reduction of hepcidin levels through inhibition of ALK2 would be a useful therapeutic strategy to combat this aspect of the disease. To test this hypothesis, a murine model of chronic kidney disease that also leads to anemia was used. Orally administered adenine metabolizes to 2,8-dihydroxyadenine, which crystalizes in the tubules of the kidney. Build-up of this metabolite causes kidney injury (nephropathy), inflammation, and subsequently anemia. Mice (typically male C57B/6 mice age 6-10 weeks) are administered adenine (maximum dose of 50 mg/kg QD) by oral gavage for 28 days. During this time, mice are monitored weekly for changes in kidney function and hematology. Anemia onset is tracked by blood draws to measure complete blood count (CBC), which includes red blood cell count, hemoglobin levels, and hematocrit. Drops in these blood parameters would be indicative of anemia. Anemia onset has been found to occur after 28 days of adenine administration, and continues for several weeks after cessation of oral adenine (Rahman et al., PLoS One, 2018). Changes in kidney function are detectable within 10 days of adenine administration (Jia et al., BMC Nephrology, 2013; Rahman et al., PLoS One, 2018), and are monitored by analysis of plasma levels of creatinine and blood urea nitrogen (BUN) (Rahman et al., PLoS One, 2018). Increases in plasma creatinine, plasma BUN, and urine protein (>2 fold) are indicative of kidney injury. Body weights are also monitored weekly as a sign of overall fitness.

Internal pilot studies indicate that kidney injury does occur within 10 days of adenine administration, hepcidin levels do increase within 3-4 weeks of adenine administration, and hemoglobin and hematocrit levels do drop after 4 weeks of adenine administration as described elsewhere (Rahman et al., PLoS One, 2018).

Studies are conducted under the supervision of a veterinarian and in compliance with guidelines and protocols established and approved by the Incyte IACUC.

Results

To investigate the ability of an ALK2 inhibitor to alleviate the anemia brought on by kidney injury, male C57BL/6 mice (Charles River Laboratories) were administered oral adenine (45 mg/kg QD) for 28 days. A cohort of mice were also administered vehicle solution to maintain a normal blood level baseline for comparison (n=10). Mice were monitored weekly for changes in blood parameters by CBC, and for changes in weight. Starting at 14 days post first administration of adenine, mice receiving adenine were dosed with either 30 mg/kg QD (n=8) or 100 mg/kg QD (n=9) Compound A, or vehicle control (n=10). Mice were dosed for 21 days, which includes 14 days after the cessation of adenine administration. Final analyses were performed one week after the last dose of Compound A, 42 days after adenine administration began. Shown in FIG. 1 are results from this experiment. The left panel shows hemoglobin levels from day 42 of the study. Mice dosed with adenine and vehicle showed signs of anemia, as indicated by decreased hemoglobin levels, while mice dosed with vehicle without adenine showed normal hemoglobin levels. Compound A dose-dependently improved hemoglobin (HGB) levels in this model. For mice that were administered adenine, the changes in HGB levels in Compound A treated mice significantly increased when compared to vehicle treated mice. In addition, reduction of anemia by Compound A resulted in increased overall health as determined by body weights as shown in the right panel in FIG. 1. Mice administered Compound A had increased weights when compared to mice administered adenine without Compound A.

Figure 2:
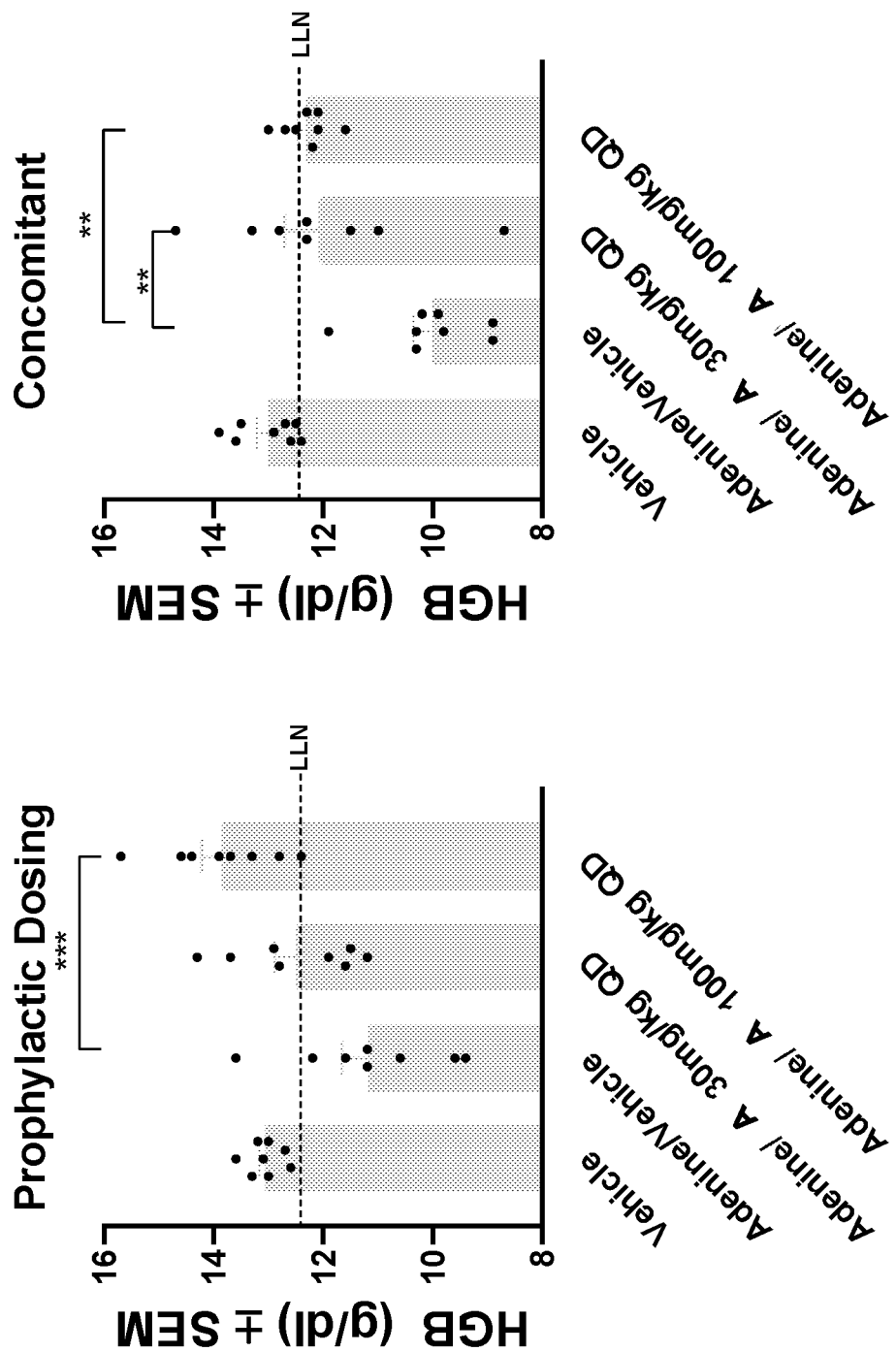
FIG. 2 shows the results of prophylactic dosing in the left panel and concomitant dosing in the right panel of the kidney disease-anemia model where p<0.01; *p<0.001 one way ANOVA with Tukey's multiple comparisons test, LLN=Lower limit of normal.

A study was performed to investigate the effects of starting the dosing of Compound A later in kidney disease progression at the point when hepcidin levels increase, at approximately of adenine administration. Male C57BL/6 mice were administered oral adenine (45 mg/kg QD) for 28 days. A cohort of mice were also administered vehicle solution to maintain a normal blood level baseline for comparison (n=8). Mice were monitored weekly for changes in blood parameters by CBC, and for changes in weight. The mice receiving adenine were dosed with either 30 mg/kg QD (n=8) or 100 mg/kg QD (n=8) Compound A, or vehicle control (n=8). Compound A dosing began at either 14 or 21 days after adenine administration began and continued for 21 days, followed by one more week until blood analysis. The dosing that began on day 14 was termed "prophylactic" as it began before the increase in hepcidin occurs. Dosing that began on day 21 was termed "concomitant" as the dosing coincided with hepcidin level increase. FIG. 2 shows the results of prophylactic dosing in the left panel and concomitant dosing in the right panel. Prophylactic dosing of Compound A led to a dose dependent increase in hemoglobin levels indicating an improvement in anemia in these animals. The 100 mg/kg QD dose of Compound A also returned hemoglobin levels that are within the normal range for C57BL/6 mice. Likewise, concomitant dosing of Compound A also resulted in significant increases in hemoglobin levels that were dose dependent. Overall, Compound A was able to improve the anemia arising in this model. Hemoglobin level improvements could be achieved while dosing prior to, or concomitantly with, the increase in hepcidin responsible for the anemia in the model.

The disclosed subject matter is not to be limited in scope by the specific embodiments and examples described herein. Indeed, various modifications of the disclosure in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

The invention claimed is:

1. A method of treating anemia in a subject in need thereof, comprising administering to the subject a compound of Formula I:

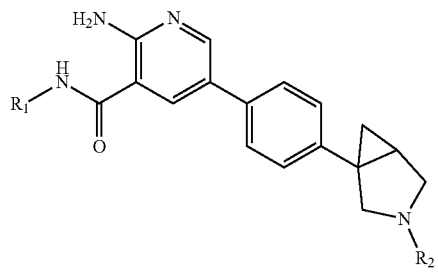

or a pharmaceutically acceptable salt thereof;
wherein
$R_1$ is bridged 5-10 membered cycloalkyl optionally substituted one, two, or three times with hydroxyl or $C_1$-$C_3$ alkoxy;
$R^2$ is selected from the group consisting of $C_1$-$C_3$ alkyl, $C_2$-$C_4$ alkenyl, $C_2$-$C_4$ alkynyl, $C_1$-$C_3$ alkoxy, 3-6 membered cycloalkyl, and 3-6 membered heterocycloalkyl, all of which are optionally substituted with $R^3$; and
$R^3$ is selected from the group consisting of hydroxy, halo, cyano, nitro, $SO_2$—$C_1$-$C_3$ alkyl, and $SO_3H$.

2. The method of claim 1, wherein $R_1$ is bridged $C_8$-cycloalkyl substituted with hydroxy; and $R_2$ is tetrahydropyran.

3. The method of claim 1, wherein the subject suffers from a myelodysplastic syndrome (MDS).

4. The method of claim 3, wherein the myelodysplastic syndrome (MDS) is selected from the group consisting of MDS with multilineage dysplasia (MDS-MLD), MDS with single lineage dysplasia (MDS-SLD), MDS with excess blasts (MDS-EB), MDS with isolated del(5q), and MDS unclassifiable (MDS-U).

5. The method of claim 1, wherein the subject suffers from multiple myeloma (MM) or myelofibrosis (MF).

6. The method of claim 1, wherein the anemia is iron-refractory iron deficiency anemia (IRIDA).

7. The method of claim 1, wherein the subject is transfusion-dependent.

8. The method of claim 1, wherein the subject is not transfusion-dependent.

9. The method of claim 1, wherein the compound of Formula I is administered orally at a dose of about 5 mg to about 500 mg once daily (QD).

10. The method of claim 1, wherein the compound of Formula I is administered as a monotherapy for anemia treatment.

11. A method of reducing hepcidin levels in a subject in need thereof, comprising administering to the subject a compound of Formula I:

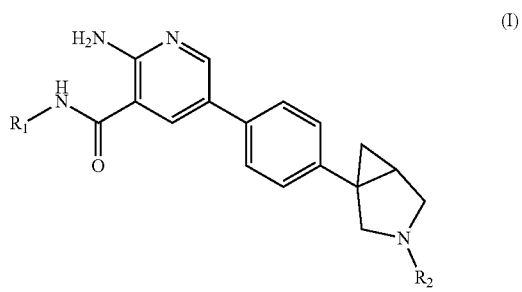

or a pharmaceutically acceptable salt thereof;
wherein
$R_1$ is bridged 5-10 membered cycloalkyl optionally substituted one, two, or three times with hydroxyl or $C_1$-$C_3$ alkoxy;
$R^2$ is selected from the group consisting of $C_1$-$C_3$ alkyl, $C_2$-$C_4$ alkenyl, $C_2$-$C_4$ alkynyl, $C_1$-$C_3$ alkoxy, 3-6 membered cycloalkyl, and 3-6 membered heterocycloalkyl, all of which are optionally substituted with $R^3$; and
$R^3$ is selected from the group consisting of hydroxy, halo, cyano, nitro, $SO_2$—$C_1$-$C_3$ alkyl, and $SO_3H$.

12. The method of claim 11, wherein $R_1$ is bridged $C_8$-cycloalkyl substituted with hydroxy; and $R_2$ is tetrahydropyran.

13. The method of claim 11, wherein the subject suffers from anemia.

14. The method of claim 13, wherein the anemia is iron-refractory iron deficiency anemia (IRIDA).

15. The method of claim 11, wherein the subject is transfusion-dependent.

16. The method of claim 11, wherein the subject is not transfusion-dependent.

17. The method of claim 11, wherein the subject suffers from a myelodysplastic syndrome (MDS).

18. The method of claim 17, wherein the myelodysplastic syndrome (MDS) is selected from the group consisting of MDS with multilineage dysplasia (MDS-MLD), MDS with single lineage dysplasia (MDS-SLD), MDS with excess blasts (MDS-EB), MDS with isolated del(5q), and MDS unclassifiable (MDS-U).

19. The method of claim 11, wherein the subject suffers from multiple myeloma (MM) or myelofibrosis (MF).

20. The method of claim 11, wherein the compound of Formula I is administered orally at a dose of about 5 mg to about 500 mg once daily (QD).

21. The method of claim 11, wherein the compound of Formula I is administered as a monotherapy to reduce hepcidin levels.

22. A method of treating chronic kidney disease (CKD)-induced anemia in a subject in need thereof, comprising administering to the subject a compound of Formula I:

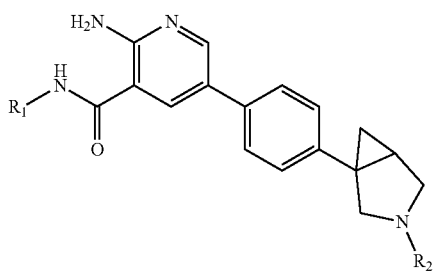

or a pharmaceutically acceptable salt thereof;
wherein
  $R_1$ is bridged 5-10 membered cycloalkyl optionally substituted one, two, or three times with hydroxyl or $C_1$-$C_3$ alkoxy;

$R^2$ is selected from the group consisting of $C_1$-$C_3$ alkyl, $C_2$-$C_4$ alkenyl, $C_2$-$C_4$ alkynyl, $C_1$-$C_3$ alkoxy, 3-6 membered cycloalkyl, and 3-6 membered heterocycloalkyl, all of which are optionally substituted with $R^3$; and $R^3$ is selected from the group consisting of hydroxy, halo, cyano, nitro, $SO_2$-$C_1$-$C_3$ alkyl, and $SO_3H$.

23. The method of claim 22, wherein $R_1$ is bridged $C_8$-cycloalkyl substituted with hydroxy; and $R_2$ is tetrahydropyran.

24. The method of claim 22, wherein the compound of Formula I is administered orally at a dose of about 5 mg to about 500 mg once daily (QD).

25. The method of claim 22, wherein the compound of Formula I is administered as a monotherapy to treat chronic kidney disease (CKD)-induced anemia.

* * * * *